United States Patent
Getts et al.

(10) Patent No.: US 7,550,264 B2
(45) Date of Patent: Jun. 23, 2009

(54) METHODS AND KITS FOR SENSE RNA SYNTHESIS

(75) Inventors: Robert Getts, Collegeville, PA (US); Kelly Sensinger, Perkasie, PA (US); James Kadushin, Gilbertsville, PA (US)

(73) Assignee: Datascope Investment Corporation, Montvale, NJ (US)

( * ) Notice: Subject to any disclaimer, the term of this patent is extended or adjusted under 35 U.S.C. 154(b) by 112 days.

(21) Appl. No.: 11/150,794

(22) Filed: Jun. 10, 2005

(65) Prior Publication Data

US 2006/0281153 A1     Dec. 14, 2006

(51) Int. Cl.
C12Q 1/68    (2006.01)
C12P 19/34   (2006.01)

(52) U.S. Cl. .................. 435/6; 435/91.2; 435/91.21; 435/91.3

(58) Field of Classification Search .............. 435/6, 435/91.2, 91.21, 91.3, 91.51
See application file for complete search history.

(56) References Cited

U.S. PATENT DOCUMENTS

| | | | |
|---|---|---|---|
| 5,130,238 A | 7/1992 | Malek et al. | |
| 5,175,270 A | 12/1992 | Nilsen et al. | |
| 5,399,491 A | 3/1995 | Kacian et al. | |
| 5,409,818 A | 4/1995 | Davey et al. | |
| 5,437,990 A | 8/1995 | Burg et al. | |
| 5,480,784 A | 1/1996 | Kacian et al. | |
| 5,484,904 A | 1/1996 | Nilsen et al. | |
| 5,487,973 A | 1/1996 | Nilsen et al. | |
| 5,545,522 A | 8/1996 | Van Gelder et al. | |
| 5,716,785 A | 2/1998 | Van Gelder et al. | |
| 5,766,849 A | 6/1998 | McDonough et al. | |
| 5,824,518 A | 10/1998 | Kacian et al. | |
| 5,888,729 A * | 3/1999 | Kacian et al. ................. | 435/6 |
| 5,891,636 A | 4/1999 | Van Gelder et al. | |
| 5,958,688 A | 9/1999 | Eberwine et al. | |
| 6,072,043 A | 6/2000 | Nilsen | |
| 6,110,687 A | 8/2000 | Nilsen | |
| 6,117,631 A | 9/2000 | Nilsen | |
| 6,582,906 B1 | 6/2003 | Cao et al. | |
| 2003/0104432 A1 | 6/2003 | Xu et al. | |
| 2004/0101844 A1 | 5/2004 | Amorese et al. | |
| 2005/0009047 A1 | 1/2005 | Erlander et al. | |

FOREIGN PATENT DOCUMENTS

| | | |
|---|---|---|
| WO | WO 90/06995 | 6/1990 |
| WO | WO 91/02818 | 3/1991 |
| WO | WO-2004/101749 A2 | 11/2004 |

OTHER PUBLICATIONS

U.S. Appl. No. 10/979,052, Getts, Robert C., et al.

(Continued)

*Primary Examiner*—Kenneth R. Horlick
*Assistant Examiner*—Joyce Tung
(74) *Attorney, Agent, or Firm*—Diehl Servilla LLC; Scott S. Servilla; Glen M. Diehl

(57) ABSTRACT

Methods and kits are provided for performing multiple rounds of sense RNA synthesis. The sense RNA molecules can be used in various research and diagnostic applications, such as gene expression studies involving nucleic acid microarrays.

20 Claims, 6 Drawing Sheets

OTHER PUBLICATIONS

Guatelli, John C., et al., "Isothermal, in vitro amplification of nucleic acids by a multienzyme reaction modeled after retroviral replication", *Proc. Natl. Acad. Sci. USA*, 87:1874-1878, Mar. 1990 *Biochemistry*.

Nilsen, Thor W., "Dendritic Nucleic Acid Structures", *J. Theor. Biol.* 187:273 (Jul. 21, 1997), 273-284.

Player, A., et al., "Laser capture microdissection, microarrays and the precise definition of a cancer cell", *Expert Rev Mol Diagn*. 4:831, (Nov. 2004), 831-840.

Stears, Robin L., "A novel, sensitive detection system for high-density microarrays using dendrimer technology", *Physiol. Genomics* 3:93, (2000), 93-99.

Van Gelder, R. N., et al., "Amplified RNA synthesis from limited quantities of heterogeneous cDNA", *Proc Natl Acad Sci USA* 87:1663, (1990), 1663-1667.

Wang, J, et al., "RNA Amplification Strategies for cDNA Microarray Experiments", *BioTechniques* 34:394, (Feb. 2003), 394-400.

\* cited by examiner

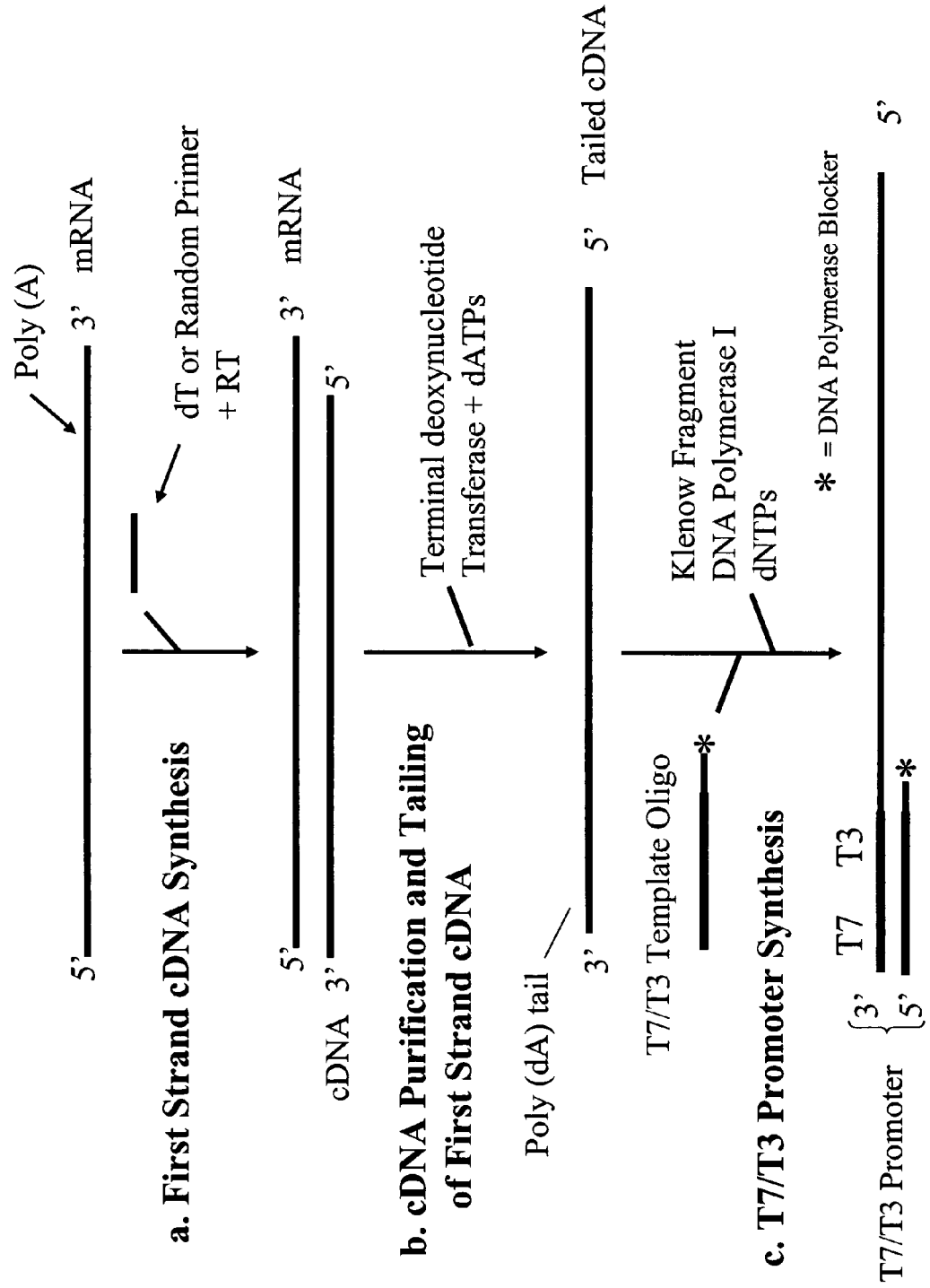

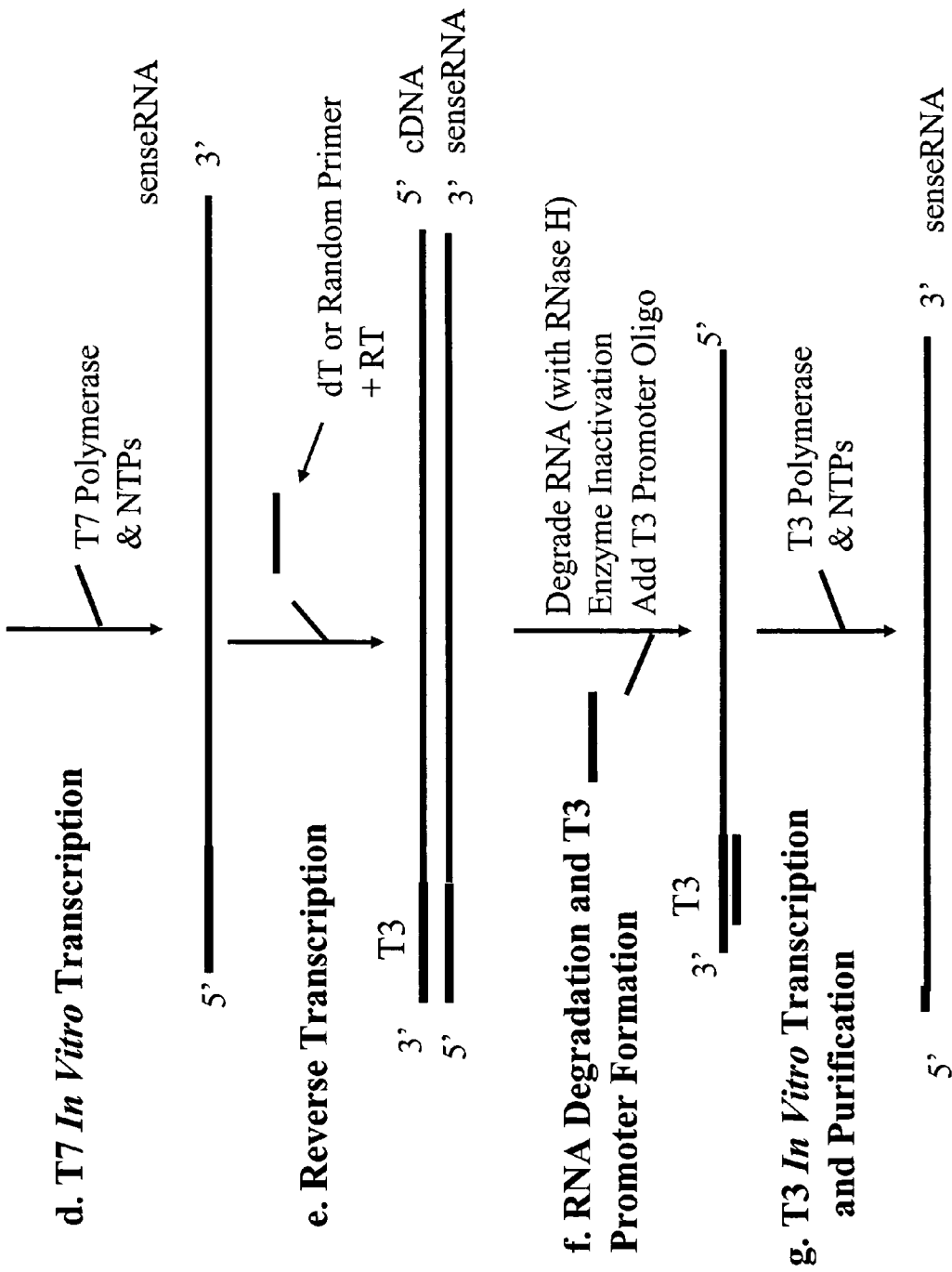

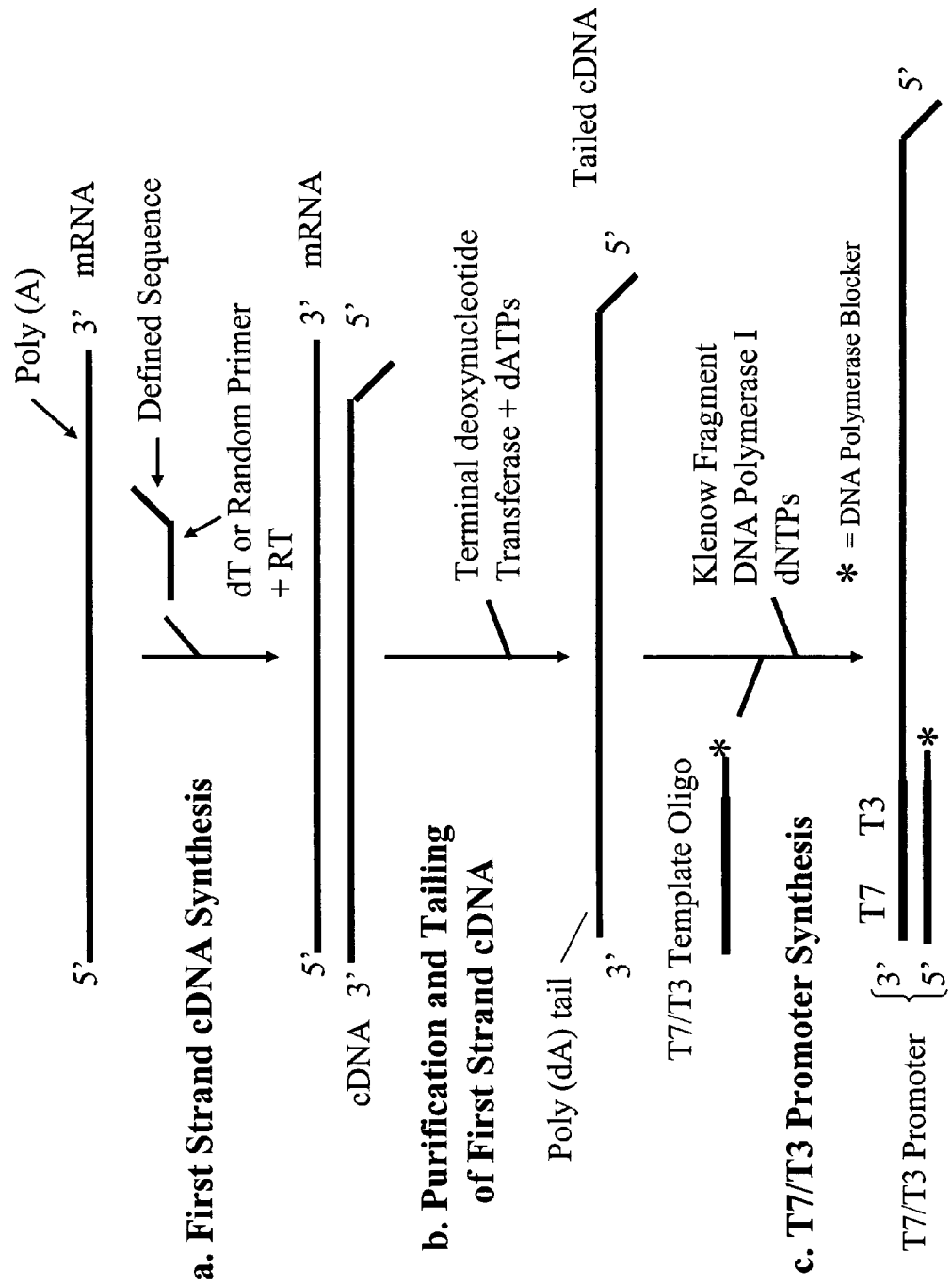

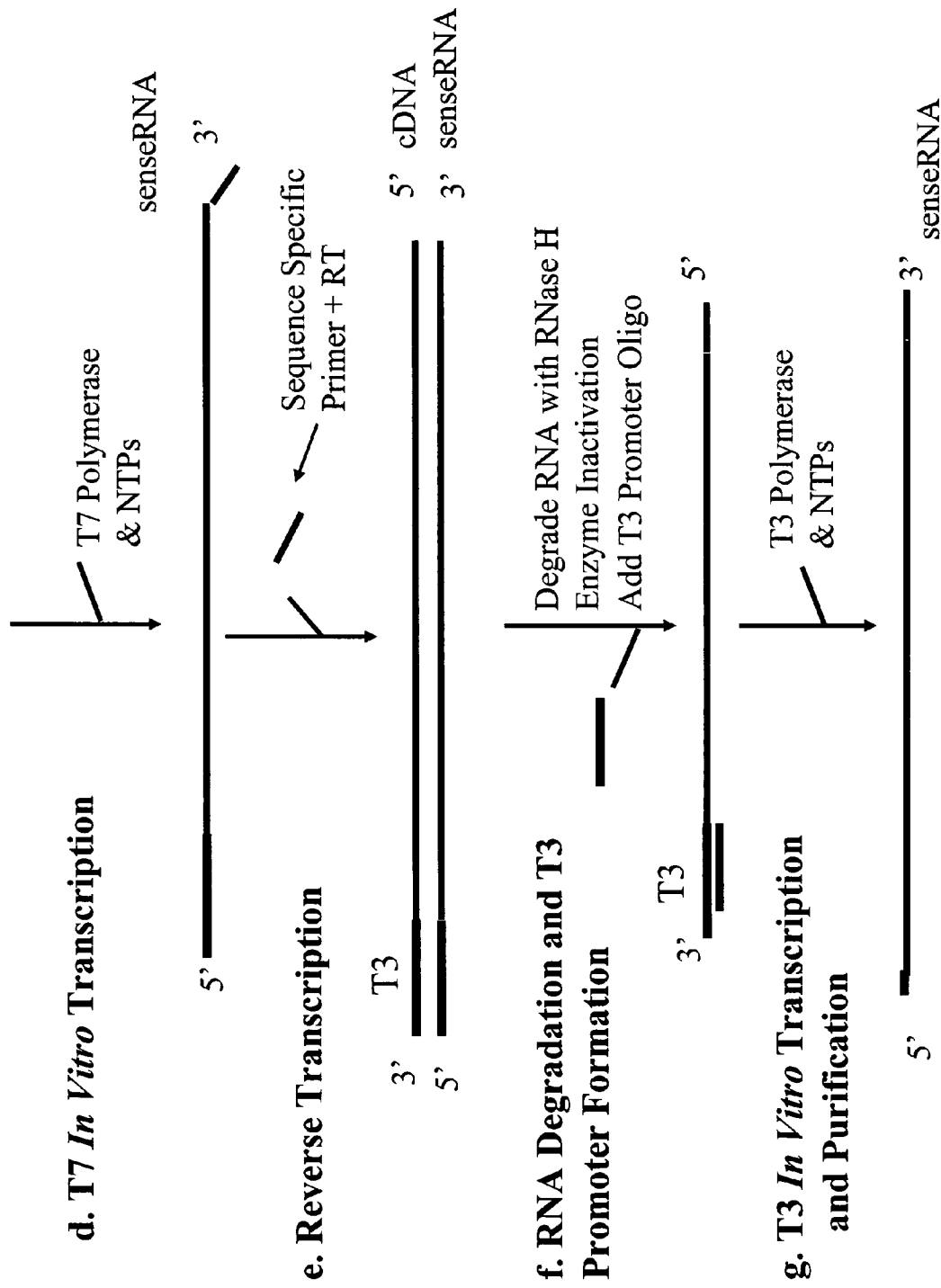

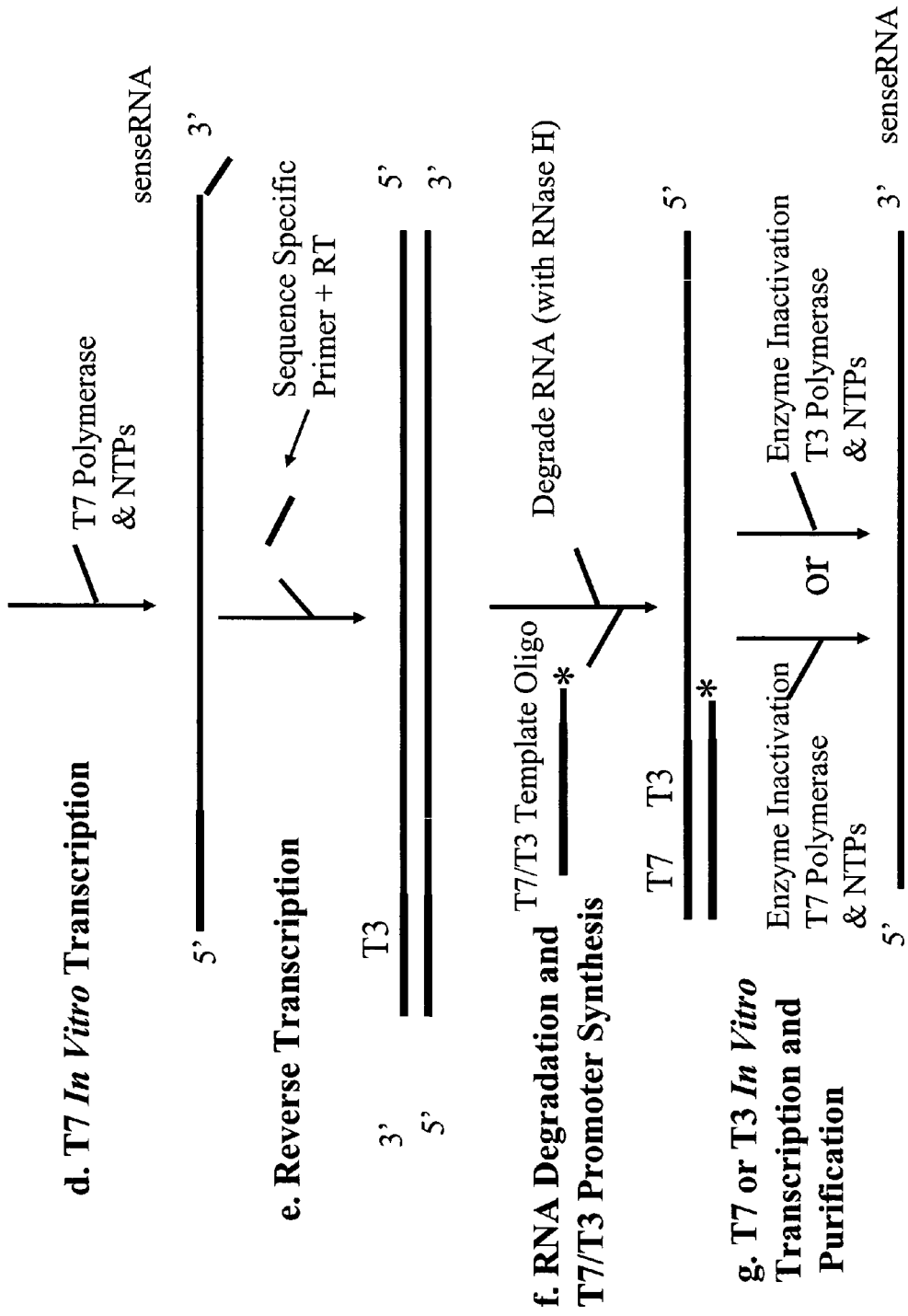

SEQUENCE LISTING

<160> NUMBER OF SEQ ID NOS: 11

<210> SEQ ID NO 1
<211> LENGTH: 20
<212> TYPE: DNA
<213> ORGANISM: T7

<400> SEQUENCE: 1
taatacgact cactataggg                     20

<210> SEQ ID NO 2
<211> LENGTH: 20
<212> TYPE: DNA
<213> ORGANISM: T3

<400> SEQUENCE: 2
aattaaccct cactaaaggg                     20

<210> SEQ ID NO 3
<211> LENGTH: 22
<212> TYPE: DNA
<213> ORGANISM: SP6

<400> SEQUENCE: 3
aatttaaggt gacactatag aa                  22

<210> SEQ ID NO 4
<211> LENGTH: 28
<212> TYPE: DNA
<213> ORGANISM: Artificial
<220> FEATURE:
<223> OTHER INFORMATION: OligodT Sequence Specific RT Primer

<400> SEQUENCE: 4
tacaaggcaa ttttttttt tttttttv                                              28

<210> SEQ ID NO 5
<211> LENGTH: 21
<212> TYPE: DNA
<213> ORGANISM: Artificial
<220> FEATURE:
<223> OTHER INFORMATION: Random Sequence Specific RT Primer
<220> FEATURE:
<221> NAME/KEY: misc_feature
<222> LOCATION: (13)..(21)
<223> OTHER INFORMATION: n is a, c, g, or t

<400> SEQUENCE: 5
tacaaggcaa ttnnnnnnnn n                                                    21

<210> SEQ ID NO 6
<211> LENGTH: 58
<212> TYPE: DNA
<213> ORGANISM: Artificial
<220> FEATURE:
<223> OTHER INFORMATION: PolydT T7T3 RNA Polymerase Promoter Template
<220> FEATURE:
<221> NAME/KEY: 3' Amino Modifier
<222> LOCATION: (58)..(58)

<400> SEQUENCE: 6
taatacgact cactataggg agaaattaac cctcactaaa gggattttt ttttttt              58

<210> SEQ ID NO 7
<211> LENGTH: 12
<212> TYPE: DNA
<213> ORGANISM: Artificial
<220> FEATURE:
<223> OTHER INFORMATION: Sequence Specific RT primer

<400> SEQUENCE: 7
tacaaggcaa tt                                                              12

<210> SEQ ID NO 8
<211> LENGTH: 22
<212> TYPE: DNA
<213> ORGANISM: Artificial
<220> FEATURE:
<223> OTHER INFORMATION: T3 Promoter Oligonucleotide

<400> SEQUENCE: 8
gaaattaacc ctcactaaag gg                                                   22

<210> SEQ ID NO 9
<211> LENGTH: 58
<212> TYPE: DNA
<213> ORGANISM: Artificial
<220> FEATURE:
<223> OTHER INFORMATION: PolydA T7T3 RNA Polymerase Promoter Template
<220> FEATURE:
<221> NAME/KEY: 3' Amino Modifier
<222> LOCATION: (58)..(58)

<400> SEQUENCE: 9
taatacgact cactataggg agaaattaac cctcactaaa gggaaaaaaa aaaaaaaa            58

<210> SEQ ID NO 10
<211> LENGTH: 28
<212> TYPE: DNA
<213> ORGANISM: Artificial

-continued

```
<220> FEATURE:
<223> OTHER INFORMATION: 3' Terminal Ribonucleotide OligodT Sequence
      Specific RT Primer
<220> FEATURE:
<221> NAME/KEY: 3' Ribonucleotide
<222> LOCATION: (28)..(28)

<400> SEQUENCE: 10
tacaaggcaa ttttttttttt tttttttv                                         28

<210> SEQ ID NO 11
<211> LENGTH: 21
<212> TYPE: DNA
<213> ORGANISM: Artificial
<220> FEATURE:
<223> OTHER INFORMATION: 3' Terminal Ribonucleotide Random Sequence
      Specific RT Primer
<220> FEATURE:
<221> NAME/KEY: Any Deoxynucleotide
<222> LOCATION: (13)..(21)
<220> FEATURE:
<221> NAME/KEY: misc_feature
<222> LOCATION: (13)..(21)
<223> OTHER INFORMATION: n is a, c, g, t or u

<400> SEQUENCE: 11
tacaaggcaa ttnnnnnnnn n                                                 21
```

US 7,550,264 B2

METHODS AND KITS FOR SENSE RNA SYNTHESIS

FIELD OF THE INVENTION

The Sequence Listing in computer readable form is hereby incorporated by reference in its entirety.

The present invention relates generally to compositions and methods for synthesizing nucleic acid molecules.

BACKGROUND OF THE INVENTION

Microarray technology has become a powerful tool for generating and analyzing gene expression profiles. Microarray expression analysis, however, generally demands large amounts of RNA that are often not available (see Wang et al., *BioTechniques* 34:394-400 (2003)). Several RNA amplification techniques have been developed to overcome this problem. These techniques, however, generally suffer from a phenomenon known as amplification bias (see, e.g., U.S. Pat. No. 6,582,906). In these cases, the amplified population of RNA molecules does not proportionally represent the population of RNA molecules existing in the original sample.

For example, in the method disclosed by Eberwine and colleagues (see, e.g., U.S. Pat. Nos. 5,545,522; 5,716,785; 5,891,636; 5,958,688; and 6,291,170), a compound oligonucleotide is utilized for the amplification, wherein the compound oligonucleotide is provided with both a T7 promoter and a primer. A cDNA copy is created of an initial mRNA transcript using the compound oliognucleotide, with subsequent second strand synthesis to create a cDNA that is double stranded. RNA amplification is conducted via the promoter portion of the compound oligonucleotide, with transcription proceeding off of the cDNA's second strand. Since the second strand is used for transcription, the Eberwine method produces amplified RNA that is antisense to the initial mRNA sequence.

The Eberwine method, however, introduces a 3' bias during each of its steps due to the incomplete processivities (i.e., the inability of an enzyme to remain attached to a nucleic acid molecule) of the enzymes utilized and the positioning of the RNA polymerase promoter (see, e.g., U.S. Pat. No. 6,582,906 and U.S. Patent Publication No. US2003/0104432). For example, the compound oligonucleotide used to produce first strand cDNA places the promoter at the 5' end of the cDNA, which corresponds to the 3' end of the message. This coupled with the inability of RNA polymerase to complete transcription of some templates (due perhaps to long polyA tail regions or interference from secondary and tertiary structures in the template) can result in a 3' bias in the amplified antisense RNA population. In addition, if second strand cDNA synthesis by DNA polymerase is incomplete, these cDNAs will lack functional promoters, resulting in a reduced representation of the original RNA molecule (or possibly a complete absence) in the amplified population.

Applicants' copending U.S. patent application Ser. No. 11/547,186, specifically incorporated herein by reference in its entirety, discloses methods for attaching single stranded promoter templates to the 3' ends of cDNA molecules which are not extendable with DNA polymerase. Following enzymatic conversion of the promoter template into a double stranded promoter with DNA polymerase, in vitro transcription is initiated by addition of RNA polymerase, resulting in the synthesis of sense RNA (sRNA) molecules having the same orientation as the original RNA molecules. Additional rounds of sRNA synthesis can be performed by reverse transcribing the sRNA molecules and re-attaching promoter templates to the second-round cDNA molecules, with subsequent enzymatic conversion into double-stranded promoters, followed by a second round of in vitro transcription with RNA polymerase.

It would be desirable to provide methods for performing additional rounds of sRNA synthesis as disclosed in U.S. patent application Ser. No. 11/547,186 without the need for re-attachment of promoter templates and subsequent enzymatic conversion into double-stranded promoters following each successive round of cDNA synthesis.

SUMMARY OF THE INVENTION

Applicants have invented methods and kits for the synthesis of sRNA molecules from various nucleic acid templates, wherein a single stranded promoter template which is not extendable with DNA polymerase comprising a first RNA polymerase recognition sequence and at least a second different RNA polymerase recognition sequence is attached to the 3' end of first-round cDNA molecules. Applicants have discovered that the use of such a promoter template allows for multiple rounds of sRNA synthesis without the need to repeat the complex series of steps associated with the re-attachment of single stranded promoter templates and subsequent enzymatic conversion into double stranded promoters following each successive round of cDNA synthesis. The double stranded promoter sequence(s) are regenerated either during second or later round reverse transcription or by addition of a single strand oligonucleotide having the promoter sequence complement immediately after reverse transcription. Specific RNA amplification is increased 100-1000-fold over previous methods without an accompanying increase in the number of non-specific artifacts.

Accordingly, one aspect of the present invention is directed to a method for synthesizing at least one sRNA molecule, comprising: providing at least one single stranded cDNA molecule having a 5' end and a 3' end; attaching an oligodeoxynucleotide tail onto the 3' end of said cDNA molecule; annealing to said oligodeoxynucleotide tail a single stranded promoter template comprising a first RNA polymerase recognition sequence and at least a second different RNA polymerase recognition sequence 3' to said first recognition sequence, wherein said single stranded promoter template is not extendable with DNA polymerase; extending said oligodeoxynucleotide tail such that said single stranded RNA polymerase promoter template is converted into a first RNA polymerase promoter and at least a second RNA polymerase promoter 3' to said first promoter; and initiating RNA transcription using an RNA polymerase which recognizes said first or second RNA polymerase promoter, thereby synthesizing at least one sRNA molecule.

Another aspect of the present invention is directed to a method for performing multiple rounds of synthesis of at least one sRNA molecule, comprising: providing at least one first round single stranded cDNA molecule having a 5' end and a 3' end; attaching an oligodeoxynucleotide tail onto the 3' end of said first round cDNA molecule; annealing to said oligodeoxynucleotide tail a single stranded promoter template comprising a first RNA polymerase recognition sequence and at least a second different RNA polymerase recognition sequence 3' to said first recognition sequence, wherein said single stranded promoter template is not extendable with DNA polymerase; extending said oligodeoxynucleotide tail such that said single stranded promoter template is converted into a first RNA polymerase promoter and at least a second RNA polymerase promoter 3' to said first promoter; initiating a first round of RNA transcription using an RNA polymerase which recognizes said first RNA polymerase promoter to produce at least one first round sRNA molecule; synthesizing at least one second round single stranded cDNA molecule from said first round sRNA molecule, said second round single stranded cDNA molecule having a 5' end and a 3' end; annealing a single stranded promoter oligonucleotide complementary to said second different RNA polymerase recognition sequence such that a second RNA polymerase promoter is formed; and initiating a second round of RNA transcription using an RNA polymerase which recognizes said second RNA polymerase promoter to produce at least one second round sRNA molecule, thereby performing multiple rounds of synthesis of at least one sRNA molecule.

Another aspect of the present invention is directed to a method for performing multiple rounds of synthesis of at least one sRNA molecule, comprising: providing at least one first round single stranded cDNA molecule having a 5' end and a 3' end; attaching an oligodeoxynucleotide tail onto the 3' end of said first round cDNA molecule; annealing to said oligodeoxynucleotide tail a single stranded promoter template comprising a first RNA polymerase recognition sequence and at least a second different RNA polymerase recognition sequence 3' to said first recognition sequence, wherein said single stranded promoter template is not extendable with DNA polymerase; extending said oligodeoxynucleotide tail such that said single stranded promoter template is converted into a first RNA polymerase promoter and at least a second RNA polymerase promoter 3' to said first promoter; initiating a first round of RNA transcription using an RNA polymerase which recognizes said first RNA polymerase promoter to produce at least one first round sRNA molecule; synthesizing at least one second round single stranded cDNA molecule from said first round sRNA molecule, said second round single stranded cDNA molecule having 5' and 3' ends; degrading said first round sRNA molecule; annealing excess single stranded promoter template to the 3' end of said second round single stranded cDNA molecule; extending the 3' end of said second round cDNA such that said excess promoter template is converted into a first RNA polymerase promoter and at least a second RNA polymerase promoter 3' to said first promoter; and initiating a second round of RNA transcription using an RNA polymerase which recognizes said first or second RNA polymerase promoter to produce at least one second round sRNA molecule, thereby performing multiple rounds of synthesis of at least one sRNA molecule and producing multiple sRNA copies.

In some embodiments, polyA tails are added to the resulting sRNA molecules to increase the number and type of downstream assays in which the sRNA molecules can be used. Preferably, the sRNA molecules are reverse transcribed into cDNA molecules for use in downstream assays.

The single stranded cDNA molecule can be provided by contacting a RNA molecule with a primer in the presence of a reverse transcriptase. Such reverse transcription primers include oligodT primers, random primers, or combinations thereof. In some embodiments, the reverse transcription primer comprises a 5' extension containing a specific nucleotide sequence. In other embodiments, the 3' terminal nucleotide of the reverse transcription primer is a nucleotide or nucleotide analog that is not a substrate for terminal deoxynucleotide transferase but can be extended by reverse transcriptase. In preferred embodiments, the reverse transcription primer comprises a 5' extension containing a specific nucleotide sequence, wherein the 3' terminal nucleotide of the reverse transcription primer is a ribonucleotide.

Another aspect of the present invention is directed to a kit for synthesizing at least one sRNA molecule, comprising: a single stranded promoter template comprising a first RNA polymerase recognition sequence and at least a second different RNA polymerase recognition sequence 3' to said first recognition sequence, wherein said single stranded promoter template is not extendable with DNA polymerase; and instructional materials for synthesizing sRNA molecules using said promoter template.

Another aspect of the present invention is directed to a kit for performing multiple rounds of synthesis of at least one sRNA molecule, comprising: a single stranded promoter template, comprising: a first RNA polymerase recognition sequence and at least a second different RNA polymerase recognition sequence 3' to said first recognition sequence, wherein said single stranded promoter template is not extendable with DNA polymerase; a single stranded promoter oligonucleotide complementary to said second RNA polymerase recognition sequence; and instructional materials for performing multiple rounds of synthesis of at least one sRNA molecule using said promoter template and promoter oligonucleotide.

In some embodiments, the kits further comprise: a reverse transcriptase; an enzyme for attaching an oligodeoxynucleotide tail onto DNA molecules; an enzyme for converting the promoter template to one or more RNA polymerase promoters; and one or more RNA polymerases.

BRIEF DESCRIPTION OF THE DRAWINGS

FIGS. 1a-g is a schematic representation that depicts an embodiment according to the methods of the present invention.

FIGS. 2a-g is a schematic representation that depicts a second embodiment according to the methods of the present invention.

DETAILED DESCRIPTION OF THE INVENTION

Figure 3:
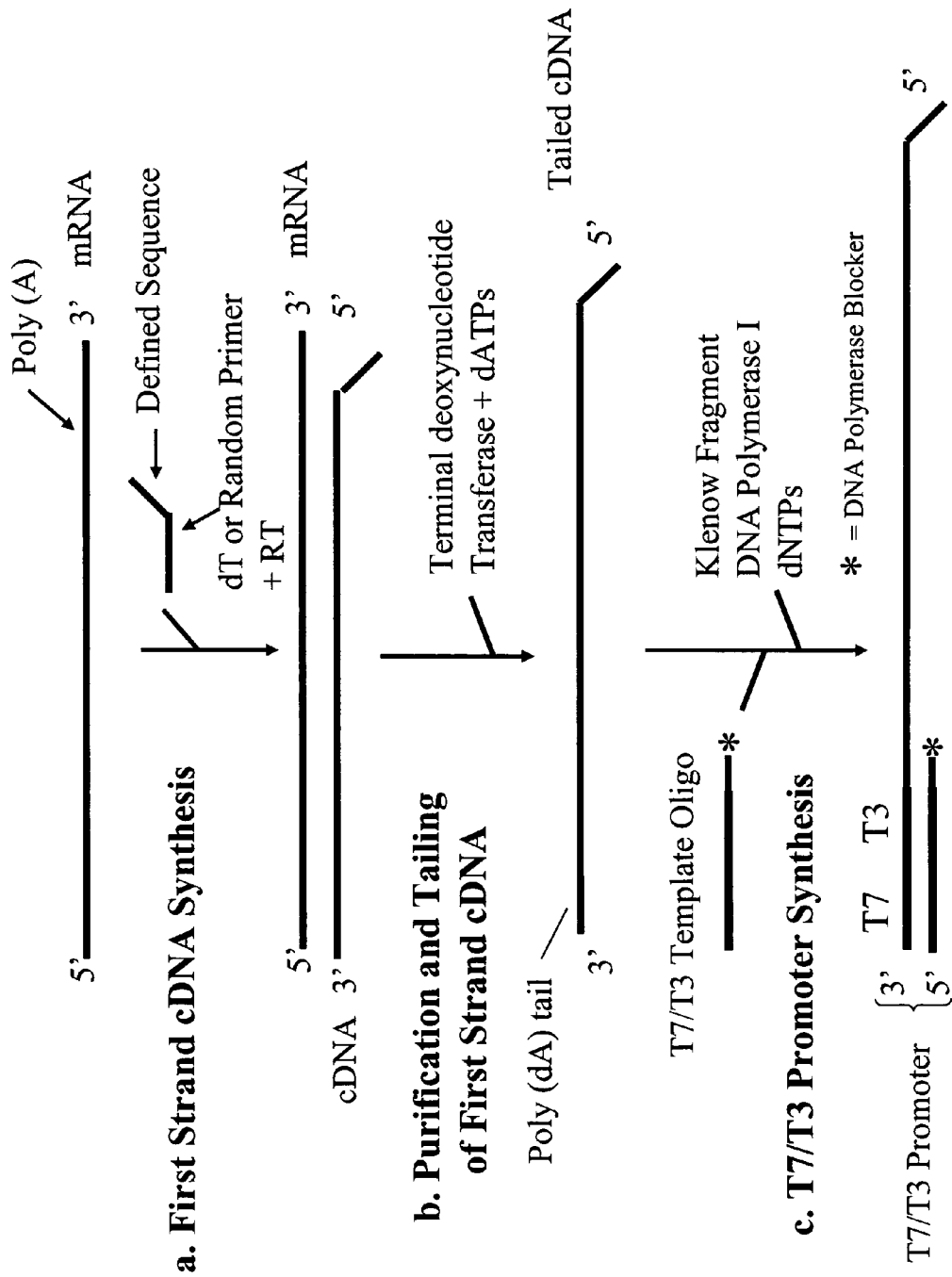
FIGS. 3a-g is a schematic representation that depicts a third embodiment according to the methods of the present invention.

The present invention relates to methods and kits for the synthesis of sRNA molecules. The terms "sRNA molecule," "RNA molecule," "DNA molecule," "cDNA molecule" and "nucleic acid molecule" are each intended to cover a single molecule, a plurality of molecules of a single species, and a plurality of molecules of different species. The methods generally comprise attaching an oligodeoxynucleotide tail onto the 3' end of at least one first round single stranded cDNA molecule; annealing to the oligodeoxynucleotide tail a single stranded promoter template comprising a first RNA polymerase recognition sequence and at least a second different RNA polymerase recognition sequence 3' to said first recognition sequence, wherein said single stranded promoter template is not extendable with DNA polymerase; extending the oligodeoxynucleotide tail such that the single stranded promoter template is converted into a first RNA polymerase promoter and at least a second RNA polymerase promoter 3' to the first promoter; initiating a first round of RNA transcription using an RNA polymerase which recognizes the first RNA polymerase promoter to produce at least one first round sRNA molecule; synthesizing at least one second round single stranded cDNA molecule having a 5' end and a 3' end from the first round sRNA molecule; degrading the first round sRNA molecule; annealing a single stranded promoter oligonucleotide complementary to the second different RNA polymerase recognition sequence such that a second RNA polymerase promoter is formed; and initiating a second round of RNA transcription using an RNA polymerase which recognizes the second RNA polymerase promoter to produce at least one second round sRNA molecule. Such robust linear amplification methods are expected to improve expression analyses involving small numbers of cells, as well as reduce the number of artifacts resulting from non-specific amplification (see Player et al., *Expert Rev. Mol. Diagn.* 4:831 (2004)).

The methods of the present invention utilize routine techniques in the field of molecular biology. Basic texts disclosing general molecular biology methods include Sambrook et al., *Molecular Cloning, A Laboratory Manual* (3d ed. 2001) and Ausubel et al., *Current Protocols in Molecular Biology* (1994).

Numerous methods and commercial kits for the synthesis of first strand cDNA molecules are well known in the art. Examples include the Superscript™ Double Strand cDNA Synthesis Kit (Invitrogen, Carlsbad, Calif.), the Array 50™, Array 350™ and Array 900™ Detection Kits (Genisphere, Hatfield, Pa.), and the CyScribe™ Post-Labelling Kit (Amersham, Piscataway, N.J.). With reference to FIG. 1, RNA molecules (e.g., mRNA, hnRNA, rRNA, tRNA, miRNA, snoRNA, non-coding RNAs) from a source of interest are used as templates in a reverse transcription reaction (see FIG. 1a). The RNA may be obtained from any tissue or cell source, including virion, prokaryotic, and eukaryotic sources found in any biological or environmental sample. Preferably, the source is eukaryotic tissue, more preferably mammalian tissue, most preferably human tissue. The methods of present invention are particularly suited for amplification of RNA from small numbers of cells, including single cells, which can be purified from complex cellular samples using, e.g., micromanipulation, fluorescence-activated cell sorting (FACS) and laser microdissection techniques (see Player et al., *Expert Rev. Mol. Diagn.* 4:831 (2004)).

Any reverse transcriptase can be used in the initial reverse transcription reaction, including thermostable, RNAse H$^+$ and RNase H$^-$ reverse transcriptases. Preferably, an RNase H$^-$ reverse trancriptase is used.

Primers for first strand cDNA synthesis can be obtained commercially or synthesized and purified using techniques well known in the art. Primers for first strand cDNA synthesis include single strand oligodeoxynucleotides comprising an oligodT tail at their 3' ends, generally ranging from about 10 to about 30 nucleotides in length, preferably from about 17 to about 24 nucleotides in length, which anneal to RNA containing a 3' polyA tail (e.g., mRNA). If the RNA of interest does not naturally contain a 3' polyA tail (e.g., miRNA), a polyA tail can be attached to the RNA molecules using polyA polymerase (PAP) in the presence of ATP. PolyA tailing kits are commercially available and include, e.g., the Poly(A) Tailing Kit (Ambion, Austin, Tex.). Three-prime blocked RNAs can be enzymatically treated to allow tailing using, e.g., calf intestinal alkaline phosphatase or RNase 3.

Alternatively, the reverse transcription reaction can be initiated using a random primer, generally ranging from about 4 to about 20 nucleotides in length, preferably from about 6 to about 9 nucleotides in length, which anneals to various positions along the length of each original mRNA transcript. One of ordinary skill in the art will recognize that the use of a random primer can ultimately result in the production of sRNA molecules that are better representative of the entire length of each original mRNA transcript than those produced using an oligodT primer. Additionally, the use of a random primer to generate cDNA in the initial steps of the disclosed methods means that RNA that would normally be exempt from amplification, such as degraded RNA or RNA derived from bacteria, can be used to produce amplified sRNA molecules.

In some embodiments, the reverse transcription primer (oligodT primer, random primer, or both) comprises a 5' extension containing a specific nucleotide sequence, generally ranging from about 6 to about 50 nucleotides in length, preferably from about 10 to about 20 nucleotides in length (see FIG. 2a). This 5' specific nucleotide sequence can be used as an initiation site for second round cDNA synthesis, as shown in FIG. 2e.

In other embodiments, the 3' terminal nucleotide of the reverse transcription primer (oligodT primer, random primer, or both) is a nucleotide or nucleotide analog that is not a substrate for terminal deoxynucleotide transferase but can be extended by reverse transcriptase, such as a ribonucleotide. Such primers are not extendable with terminal deoxynucleotidyl transferase (TdT), and thus will not be tailed and amplified in the steps shown in FIGS. 1c-1f. In preferred embodiments, the reverse transcription primer comprises a 5' extension containing a specific nucleotide sequence, wherein the 3' terminal nucleotide of the reverse transcription primer is a ribonucleotide.

Following first strand cDNA synthesis, the resulting first round cDNA molecules are generally purified (see FIG. 1b). While not degrading the RNA prior to cDNA purification is preferred, cDNA that has been purified following RNA degradation works equally well in the methods of the present invention. Any method that degrades RNA can be used, such as treatment with NaOH or RNase H (whether supplied in the form of a RNase H$^+$ reverse transcriptase or as a separate enzyme). Alternatively, the RNA can be left intact, with the first round cDNA molecules purified from RNA/cDNA duplexes. Numerous methods and kits exist for the purification of DNA molecules, including, e.g., the MinElute™ PCR Purification Kit (Qiagen, Valencia, Calif.). If a reverse transcription primer is used for first strand cDNA synthesis in which the 3' terminal nucleotide is a ribonucleotide, DNA purification can be omitted. This may reduce sample loss and increase amplification yield, which is particularly important when manipulating RNA from small numbers of cells.

Following first round cDNA purification, a single stranded oligodeoxynucleotide tail is attached to the 3' end of the cDNA molecules (see FIG. 1b). The use of such oligodeoxynucleotide tails allows whole populations of nucleic acid molecules to be amplified, rather than just specific sequences. The oligodeoxynucleotide tail can be incorporated by any means that attaches deoxynucleotides to DNA. Preferably, the oligodeoxynucleotide tail is attached to the cDNA using terminal deoxynucleotidyl transferase, or other suitable enzyme, in the presence of appropriate deoxynucleotides. Preferably, the oligodeoxynucleotide tail is a homopolymeric tail (i.e., polydA, polydG, polydC, or polydT). Preferably, the oligodeoxynucleotide tail is a polydA tail, generally ranging from about 3 to greater than 500 nucleotides in length, preferably from about 20 to about 100 nucleotides in length. Applicants have found that the use of a polydA tail reduces the number of artifacts resulting from non-specific amplification.

Following attachment of the single stranded oligonucleotide tail to the 3' ends of the first round cDNA molecules, a single stranded promoter template is attached to the 3' oligodeoxynucleotide tail (see FIG. 1b). This is accomplished through complementary base pairing between the 3' oligodeoxynucleotide tail and a complementary series of deoxynucleotides present at the 3' end of the single stranded promoter template. For example, if oligonucleotide tail is a polydA tail, the promoter template will contain a series of thymidine bases at its 3' end, generally ranging from about 3 to greater than 50 nucleotides in length, preferably from about 10 to about 30 nucleotides in length. The particular nucleotide sequence of the 3' promoter template sequence does not have to be perfectly complementary to the particular nucleotide sequence of the 3' oligodeoxynucleotide tail, nor does the length of the 3' promoter template sequence need to match exactly the length of the 3' oligodeoxynucleotide tail, for the sequences to be considered complementary to each other. Those of skill in the art will recognize that what is required is that there be sufficient complementarity between the two sequences so that the promoter template can anneal to the oligodeoxynucleotide tail at the 3' end of the cDNA molecules.

The single stranded promoter template contains at its 5' end a first RNA polymerase recognition sequence and at least a second different RNA polymerase recognition sequence 3' to the first recognition sequence (i.e., a "tandem promoter template"). The term "RNA polymerase recognition sequence" is intended to cover both single stranded and double stranded nucleotide sequences. When in single stranded form, the nucleotide sequence corresponds to the non-template strand of a double-stranded RNA polymerase promoter. When in double stranded form, the nucleotide sequences correspond to both the template and non-template strands of a double-stranded RNA polymerase promoter. Any RNA polymerase recognition sequence can be used, so long as it is specifically recognized by an RNA polymerase. Preferably, the RNA polymerase recognition sequence used is recognized by a bacteriophage RNA polymerase, such as T7, T3, or SP6 RNA polymerase. An exemplary T7 RNA polymerase recognition sequence is TAATACGACTCACTATAGGG (SEQ ID NO: 1). An exemplary T3 RNA polymerase recognition sequence is AATTAACCCTCACTAAAGGG (SEQ ID NO: 2). An exemplary SP6 RNA polymerase recognition sequence is AATTTAAGGTGACACTATAGAA (SEQ ID NO: 3).

The single stranded promoter template is also blocked at its 3' end such that it is not extendable with DNA polymerase. As such, the addition of a DNA polymerase (such as Klenow DNA polymerase) and dNTPs extends the single stranded oligonucleotide tail and converts the single stranded promoter template into a first double stranded RNA polymerase promoter and at least a second different double stranded RNA polymerase promoter, but does not catalyze the synthesis of second strand cDNA (see FIG. 1c). The promoter template can be blocked by any means that renders it incapable of being extended with DNA polymerase, such as by including terminal blocking groups, compounds, or moieties either attached during or after synthesis. Preferably, the promoter template is blocked with a 3' amino modifier, a 3' deoxyterminator, or a 3' dideoxyterminator. A suitable blocker should not be restricted to any of those described herein and can include any moiety that will prevent DNA polymerase from extending the 3' terminus of the promoter template.

In some embodiments, rather than converting a single stranded promoter template into a double stranded RNA polymerase promoter using DNA polymerase, a double stranded RNA polymerase promoter having a template strand and a non-template strand is attached to the 3' ends of the first round cDNA molecules by DNA ligation (see Applicant's copending International Patent Application No. PCT/US2004/014325, specifically incorporated herein by reference in its entirety). The double stranded RNA polymerase promoter contains at its 5' end (relative to the non-template strand) a first RNA polymerase recognition sequence and at least a second different RNA polymerase recognition sequence 3' to the first recognition sequence. Attachment of the promoter is facilitated by complementary base pairing between the 3' oligodeoxynucleotide tail of the cDNA molecule (e.g., polydA tail) and an overhang sequence at the 3' end of the non-template strand of the double stranded RNA polymerase promoter that contains a complementary series of nucleotides (i.e., polydT overhang). Once properly positioned, the double stranded promoter is attached to the cDNA molecule by ligation of the 5' end of the template strand of the promoter to the 3' end of the oligodeoxynucleotide tail. Any DNA ligase can be used in the ligation reaction. Preferably, the DNA ligase is T4 DNA ligase.

Although the methods of current invention are preferably performed in the absence of second strand cDNA synthesis, one of skill in the art will recognize that second strand cDNA can be optionally synthesized during conversion of the single stranded promoter template into double stranded RNA polymerase promoters by using a random primer. The random primer will anneal at various positions along the first strand cDNA and be extended by DNA polymerase during promoter synthesis. The various second strand cDNA fragments can be optionally ligated together to form a single second strand cDNA molecule. Such second strand cDNA molecules may stabilize (i.e., remove secondary and tertiary structure) the first strand cDNA during in vitro transcription, resulting in a higher yield of sRNA molecules.

Following conversion of the single stranded promoter template into double stranded RNA polymerase promoters, in vitro transcription is initiated by the addition of ribonucleotides and a RNA polymerase that recognizes the first promoter (see FIG. 1d). Methods and kits for performing in vitro transcription are well known in the art and include the MEGAscript™ Transcription Kit (Ambion) and the AmpliScribe™ High Yield Transcription Kits (Epicentre Technologies, Madison, Wis.).

The resulting first round sRNA molecules can be subjected to a second round of synthesis by first reverse transcribing the sRNA molecules into first strand cDNA molecules as described above (see FIG. 1e). For example, sRNA molecules produced from oligodT-primed first strand cDNA (i.e., first round sRNA molecules) will have regenerated polyA tails at their 3' ends, which can serve as priming sites for a second round of oligodT-primed first strand cDNA synthesis. Additionally, and for first round sRNA molecules produced from random-primed first strand cDNA, 3' polyA tails can be added to the sRNA molecules for oligodT-primed first strand cDNA synthesis, or random primer-mediated reverse transcription can again be performed to produce second round cDNA. Combinations and mixtures of oligodT and random primers can also be used for second round cDNA synthesis.

If the first reverse transcription primer used in FIG. 2a comprises a 5' extension containing a specific nucleotide sequence, the first round sRNA molecules will contain a defined complementary nucleotide sequence at their 3' ends. Reverse transcription can be initiated using a second reverse transcription primer comprising a nucleotide sequence complementary to this defined nucleotide sequence (i.e., "corresponding" to the specific nucleotide sequence of the 5' extension) (See FIG. 2e). Only first round sRNA molecules containing the defined nucleotide sequence will be reversed transcribed, resulting in a lower number of non-specific artifacts. Alternatively, second round reverse transcription can be initiated using the oligodT primer and/or random primer used for first round cDNA synthesis (or another suitable primer).

Following second round cDNA synthesis, the RNA is degraded using NaOH or preferably RNase H prior to optional purification of the first strand cDNA molecules (see FIG. 1*f*). Similarly, an RNase H+ reverse transcriptase can be used, such as MMLV (Promega, Madison, Wis.).

Following RNA degradation, a single stranded promoter oligonucleotide complementary to the second different RNA polymerase recognition sequence is annealed to the second round cDNA molecules through complementary base pairing (see FIG. 1*f*). This base pairing forms a second RNA polymerase promoter, from which a second round of in vitro transcription (i.e., second round sRNA molecules) is initiated by the addition of ribonucleotides and a RNA polymerase that recognizes the second promoter (see FIG. 1*g*). By incorporating additional different RNA polymerase recognition sequences into the promoter template, additional rounds of sRNA synthesis can be performed as described (e.g., third round sRNA molecules, etc.). Further, by heat inactivating all enzymes between steps or before addition of RNA polymerase, using methods familiar to one skilled in the art, linear, rather than exponential, amplification can be maintained. Such linear amplification is better suited for various downstream applications, such as gene expression studies. It should be understood that unless otherwise specified, all enzyme activity is terminated either before the next enzymatic manipulation or prior to adding RNA polymerase.

In some embodiments, rather than inactivating the reverse transcriptase following second round cDNA synthesis and annealing a single stranded promoter oligonucleotide complementary to the second different RNA polymerase recognition sequence, the RNA component is degraded using Rnase H and the first double stranded promoter is regenerated by the binding of excess single stranded promoter template to the 3' ends of the second round cDNA molecules and the DNA-dependent DNA polymerase activity of the still-active reverse transcriptase (see FIG. 3*f*). A second round of in vitro transcription can then be initiated by the addition of an RNA polymerase that recognizes either the first or second promoter (see FIG. 3*g*). Again, the reverse transcriptase is generally heat inactivated just prior to addition of RNA polymerase to maintain the linearity of the amplification. Those of skill in the art will recognize that the single stranded promoter template in this embodiment need not contain two RNA polymerase recognition sequences in tandem. Rather, the promoter template can contain a single RNA polymerase recognition sequence (see Applicants' copending U.S. patent application Ser. No. 11/547,186), which can be used in place of the tandem promoter template in FIG. 3*c* and FIG. 3*f* to produce templates for first and second round sRNA synthesis.

The sRNA molecules produced by the methods of the present invention can be used directly for any purpose mRNA is typically used for, including gene expression studies, genetic cloning, subtractive hybridization, and other techniques familiar to one experienced in the art. Preferably, the sRNA molecules are reverse transcribed into cDNA molecules using random primers, oligodT primers, or combinations thereof. The reverse transcription reaction can be performed directly in the presence of detectably labeled nucleotides, such as fluorescently labeled nucleotides. Such nucleotides include nucleotides labeled with Cy3 and Cy5.

Alternatively, the cDNA molecules are labeled indirectly. For example, the reverse transcription reaction can be performed in the presence of biotinylated or amino allyl nucleotides (e.g., amino allyl UTP), followed by coupling to a NHS ester label (e.g., Cy dye). Preferably, the cDNA molecules are labeled indirectly using 3DNA™ dendrimer technology (Genisphere, Hatfield, Pa.). Dendritic reagents are further described in Nilsen et al., *J. Theor. Biol.*, 187:273 (1997); in Stears et al., *Physiol. Genomics*, 3:93 (2000); and in various U.S. patents, such as U.S. Pat. Nos. 5,175,270; 5,484,904; 5,487,973; 6,072,043; 6,110,687; and 6,117,631, each specifically incorporated herein by reference in its entirety.

The sRNA molecules can also be used in cRNA amplification procedures to produce labeled antisense RNA (asRNA) molecules. For example, using the method of Eberwine et al. (see, e.g., Van Gelder et al., *Proc. Natl. Acad. Sci. USA* 87:1663 (1990); U.S. Pat. Nos. 5,545,522; 5,716,785; 5,891,636; 5,958,688; and 6,291,170, each specifically incorporated herein by reference in its entirety), a T7 promoter primer can be used to reverse transcribe the sRNA molecules. Following second strand cDNA synthesis, RNA transcription is initiated using T7 RNA polymerase, producing amplified asRNA molecules. Such asRNA molecules can be labeled directly during synthesis by incorporating labeled nucleotides (e.g., Cy-labeled nucleotides), or can be indirectly labeled by e.g., incorporating a biotinylated or amino allyl nucleotide (e.g., amino allyl UTP), followed by coupling to a NHS ester label (e.g., Cy dye).

The labeled single stranded cDNA and asRNA molecules produced from the sRNA molecules of the present invention are useful as reagents for gene expression studies. The labeled cDNA and asRNA molecules can be annealed to a nucleic acid microarray containing complementary polynucleotides (e.g., probes). As used herein, "microarray" is intended to include any solid support containing nucleic acid probes, including slides, chips, membranes, beads, and microtiter plates. Examples of commercially available microarrays include the GeneChip® microarray (Affymetrix, Santa Clara, Calif.), CodeLink™ microarray (Amersham Biosciences, Piscataway, N.J.), Agilent (Palo Alto, Calif.) Oligo microarray, and OciChip™ microarray (Ocimum Biosolutions, Indianapolis, Ind.).

The methods and compositions of the present invention can be conveniently packaged in kit form. Such kits can be used in various research and diagnostic applications. For example, methods and kits of the present invention can be used to facilitate a comparative analysis of expression of one or more genes in different cells or tissues, different subpopulations of the same cells or tissues, different physiological states of the same cells or tissue, different developmental stages of the same cells or tissue, or different cell populations of the same tissue. Such analyses can reveal statistically significant differences in the levels of gene expression, which, depending on the cells or tissues analyzed, can then be used to facilitate diagnosis of various disease states.

A wide variety of kits may be prepared according to present invention. For example, a kit may include a single stranded promoter template that is not extendable with DNA polymerase comprising a first RNA polymerase recognition sequence and at least a second different RNA polymerase recognition sequence 3' to the first recognition sequence; and instructional materials for synthesizing sRNA molecules using the promoter template. For performing additional rounds of sRNA synthesis, the kit can further include a single stranded promoter oligonucleotide complementary to the second RNA polymerase recognition sequence of the promoter template and the appropriate instructional materials. While the instructional materials typically comprise written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. Such media may include addresses to internet sites that provide such instructional materials.

The kits of the present invention may further include one or more of the following components or reagents: a reverse transcriptase; an RNase inhibitor; an enzyme for attaching an oligodeoxynucleotide tail onto DNA molecules (e.g., terminal deoxynucleotidyl transferase); an enzyme for attaching an oligoribonucleotide tail onto RNA molecules (e.g., polyA polymerase); an enzyme for converting the promoter template to one or more RNA polymerase promoters (e.g., Klenow enzyme); and one or more RNA polymerases (RNAse H$^+$, RNase H$^-$ or both). Additionally, the kits may include buffers, primers (e.g., oligodT primers, random primers), nucleotides, labeled nucleotides, RNase-free water, containers, vials, reaction tubes, and the like compatible with the synthesis of sRNA molecules according to the methods of the present invention. The components and reagents may be provided in containers with suitable storage media.

Specific embodiments according to the methods of the present invention will now be described in the following examples. The examples are illustrative only, and are not intended to limit the remainder of the disclosure in any way.

EXAMPLES

Example 1

First Strand cDNA Synthesis

For each RNA sample, purified using the RNAqueous® Kit (Ambion), the following RNA/primer mix was prepared on ice:

1-8 µl total RNA (not exceeding 2 ng)

2 µl first round oligodT sequence specific RT primer (50 ng/µl) (5'-TAC AAG GCA ATT TTT TTT TTT TTT TTT V-3', where V=C, G or A deoxyribonucleotides; SEQ ID NO: 4)

1 µl first round random sequence specific RT primer (2× by mass of RNA) (5'-TAC AAG GCA ATT NNN NNN NNN-3, where N=A, G, C or T deoxyribonucleotides at random; SEQ ID NO: 5)

RNase-free water to 11 µl

The first round RT primers comprise a 5' extension containing a specific nucleotide sequence that serves as binding sites for second round RT primers (see FIG. 2a). The RNA/primer mixture was heated at 80° C. for 10 minutes and immediately cooled on ice for 1-2 min. The mixture was then mixed with 9 µl of a Master Mixture solution to bring the final volume to 20 µl containing 1×RT buffer (50 mM Tris-HCl (pH 8.3), 75 mM KCl, 3 mM MgCl$_2$), 10 mM dithiothreitol (DTT), 0.5 mM each dNTP, 10 U Superase-In™ (Ambion), and 200 U Superscript™ II reverse transcriptase (Invitrogen). The mixture was briefly centrifuged and incubated at 42° C. for 2 hrs. Following a brief centrifugation, the reaction was adjusted to 100 µl with 1×TE (10 mM Tris-HCl, pH 8.0, 1 mM EDTA).

cDNA Purification

The reaction was purified using the MinElute™ PCR Purification Kit (Qiagen) according to the manufacturer's protocol. Briefly, the cDNA reaction was adjusted to 600 µl with PB buffer provided by the manufacturer. The cDNA reaction was applied to the MinElute™ column and microfuged for 1 minute. The flow-through in the collection tube was discarded, and the column washed with 750 µl PE buffer provided by the manufacturer. The flow-through in the collection tube was discarded, and the column washed with 500 µl 80% ethanol. The flow-through in the collection tube was discarded, and the column microfuged with the cap open for 5 minutes to dry the resin. The column was placed in a clean 1.5 ml microfuge tube, and the column membrane incubated with 10 µl EB buffer provided by the manufacturer for 2 minutes at room temperature. The first strand cDNA molecules were eluted by microfugation for 2 minutes.

Tailing of First Strand cDNA

The first strand cDNA molecules were heated at 80° C. for 10 minutes and immediately cooled on ice for 1-2 min. The cDNA molecules in 10 µl were then mixed with 10 µl of a Master Mixture solution to bring the final volume to 20 µl containing 1× Tailing buffer (10 mM Tris-HCl, pH 7.0, 10 mM MgCl$_2$), 0.04 mM dATP, and 15 U terminal deoxynucleotidyl transferase (Roche Diagnostics, Indianapolis, Ind.). The mixture was briefly centrifuged and incubated at 37° C. for 2 min. The reaction was stopped by heating at 80° C. for 10 min and cooled at room temperature for 1-2 minutes.

T7/T3 Promoter Synthesis

Two µl of T7T3 RNA polymerase promoter template (50 ng/µl) containing a 3' amino modifier (5'-TAA TAC GAC TCA CTA TAG GGA GAA ATT AAC CCT CAC TAA AGG GAT TTT TTT TTT TTT T-3'; SEQ ID NO: 6) was added to the oligodA-tailed cDNA molecules and the mixture incubated at 37° C. for 10 min to anneal the strands. This template, which is not extendable with DNA polymerase, contains a T7 RNA polymerase recognition sequence and a T3 RNA polymerase recognition sequence immediately 3' to the T7 sequence. The tailed cDNA/promoter template mixture in was then mixed with 3 µl of a Master Mixture solution to bring the final volume to 25 µl containing 1× Polymerase buffer (10 mM Tris-HCl, pH 7.0, 10 mM MgCl$_2$), 0.4 mM each dNTP, and 2 U Large DNA polymerase I (Klenow enzyme) (Roche). The mixture was briefly centrifuged and incubated at room temperature for 30 min. The reaction was stopped by heating at 65° C. for 10 min and placed on ice.

T7 In Vitro Transcription

One-half of the promoter synthesis reaction (12.5 µl) was heated at 37° C. for 10-15 min to re-anneal the T7T3 promoter strands and then mixed with 12.5 µl of a Master Mixture solution to bring the final volume to 25 µl containing 1× Reaction buffer, 7.5 mM each rNTP, and 2 µl T7 RNA polymerase (MEGAscript™ Transcription Kit, Ambion). The mixture was briefly centrifuged and incubated in a thermocycler with a heated lid at 37° C. for 4-16 hrs. Alternatively, the mixture was incubated in a 37° C. heat block for 15 min, followed by incubation in an air hybridization oven at 37° for 4-16 hrs. It is essential to avoid evaporation and condensation of the reaction during this step.

Reverse Transcription of sRNA

Twenty-five µl of sRNA was mixed with 1 µl second round sequence specific RT primer (500 ng/µl) (5'-TAC AAG GCA ATT-3'; SEQ ID NO: 7) and heated at 80° C. for 10 min. The second round primer contains a nucleotide sequence corresponding to the specific nucleotide sequence of the 5' extension of the first round RT primers (see FIG. 2e). The reaction was immediately iced for 2 min, briefly centrifuged, and returned to ice. One µl dNTP mix (10 mM each) and 1 µl Superscript™ II reverse transcriptase (200 U/µl) was added, and the RT reaction incubated at 42° C. for 1 hr. One µl RNase H (2 U/µl) (Invitrogen) was added, and the reaction incubated at 37° C. for 20 min. The reaction was incubated at 65° C. to stop enzyme activity.

T3 Promoter Formation

Two µl of T3 promoter oligonucleotide (50 ng/µl) (5'-GAA ATT AAC CCT CAC TAA AGG G-3'; SEQ ID NO: 8) was added to the second round cDNA reaction. The T3 oligonucleotide is complementary to the T3 RNA polymerase recognition sequence of the initial T7T3 RNA polymerase promoter template. The reaction was incubated at 37° for 10 min to anneal the strands.

T3 In Vitro Transcription

The promoter synthesis reaction was mixed with 19 μl of a Master Mixture solution to bring the final volume to 25 μl containing 1× Reaction buffer, 7.5 mM each rNTP, and 2 μl T3 RNA polymerase (MEGAscript™ Transcription Kit, Ambion). The mixture was briefly centrifuged and incubated in a thermocycler with a heated lid at 37° C. for 4-16 hrs. Alternatively, the mixture was incubated in a 37° C. heat block for 15 min, followed by incubation in an air hybridization oven at 37° for 4-16 hrs. It is essential to avoid evaporation and condensation of the reaction during this step.

sRNA Purification and Quantitation

The second round sRNA molecules were purified using the RNeasy Kit (Qiagen) following manufacturer's protocol for RNA cleanup. The purified sRNA molecules were eluted twice in 50 μl RNase-free water and quantified by UV-spectrophotometry in 0.1×TE Buffer, pH 8.0 at a wavelength ratio of 260/280.

Replicate amplifications were performed starting with 1 ng of total RNA or water alone (negative control). On average, 25 μg of amplified sRNA was recovered after amplifying 1 ng of total RNA vs. 0.5-4 μg of non-specific amplification product when using only water in the reverse transcription reaction in place of RNA.

Example 2

Each RNA sample was amplified as described in Example 1, except that only the oligo dT sequence specific primer was used for first round cDNA synthesis. The following RNA/primer mix was prepared on ice:
- 1-8 μl total RNA (not exceeding 2 ng)
- 2 μl first round oligodT sequence specific RT primer (50 ng/μl) (5'-TAC AAG GCA ATT TTT TTT TTT TTT TTT V-3', where V=C, G or A; SEQ ID NO: 4)
- RNase-free water to 11 μl Replicate amplifications were performed starting with 1 ng of total RNA or water alone (negative control). On average, 8-10 μg of amplified sRNA was recovered after amplifying 1 ng of total RNA vs. 0.5-4 μg of non-specific amplification product when using only water in the reverse transcription reaction in place of RNA.

Example 3

Each RNA sample was amplified as described in Example 1, except that only the random sequence specific primer was used for first round cDNA synthesis. The following RNA/primer mix was prepared on ice:
- 1-8 μl total RNA (not exceeding 2 ng)
- 1 μl first round random sequence specific RT primer (2× by mass of RNA) (5'-TAC AAG GCA ATT NNN NNN NNN-3, where N=A, G, C or T at random; SEQ ID NO: 5)
- RNase-free water to 11 μl Replicate amplifications were performed starting with 1 ng of total RNA or water alone (negative control). On average, 20-25 μg of amplified sRNA was recovered after amplifying 1 ng of total RNA vs. 0.5-4 μg of non-specific amplification product when using only water in the reverse transcription reaction in place of RNA.

Example 4

Each RNA sample was amplified as described in Example 1, except that dTTP was substituted for dATP in the cDNA tailing step using TdT and the corresponding 3'amino-modified T7T3 RNA polymerase promoter template used was 5'-TAA TAC GAC TCA CTA TAG GGA GAA ATT AAC CCT CAC TAA AGG GAA AAA AAA AAA AAA A-3' (SEQ ID NO: 9).

Replicate amplifications were performed starting with 1 ng of total RNA or water alone (negative control). On average, 60-70 μg of amplified sRNA was recovered after amplifying 1 ng of total RNA vs. 2-8 μg of non-specific amplification product when using only water in the reverse transcription reaction in place of RNA. While it is less desirable to have more non-specific amplification product, certain applications, such as subtractive cloning and others familiar to one experienced in the art, are not negatively impacted by the non-specific product, and in fact may be easier to perform since the same extension (polydA) is on both ends of the product.

Example 5

Each RNA sample was amplified as described in Example 1, except that 3' terminal ribonucleotide sequence specific primers were used in place of primers consisting solely of deoxyribonucleotides for first round cDNA synthesis. The following RNA/primer mix was prepared on ice:
- 1-8 μl total RNA (not exceeding 2 ng)
- 2 μl first round oligodT sequence specific RT primer (50 ng/μl) (5'-TAC AAG GCA ATT TTT TTT TTT TTT TTT V-3', where V=C, G or A ribonucleotides; SEQ ID NO: 10)
- 1 μl first round random sequence specific RT primer (2× by mass of RNA) (5'-TAC AAG GCA ATT NNN NNN NNN-3, where the first 8 N=A, G, C or T deoxyribonucleotides at random and the final N=A, G, C or U ribonucleotides at random; SEQ ID NO: 11)
- RNase-free water to 11 μl Replicate amplifications were performed starting with 1 ng of total RNA or water alone (negative control). On average, 20 μg of amplified sRNA was recovered after amplifying 1 ng of total RNA vs. 0.2-0.5 μg of non-specific amplification product when using only water in the reverse transcription reaction in place of RNA.

Example 6

Each RNA sample was amplified as described in Example 5, except that first round cDNA purification was performed using YM100 Microconcentrators (Millipore, Billerica, Mass.) in place of the MinElute™ PCR Purification Kit. The 100 μl diluted reverse transcription reaction was applied to the sample reservoir. The tube cap was secured and the unit centrifuged for 6 minutes at 13,000×g. Two-hundred μl of 1×TE buffer, pH 8.0 was added to the sample reservoir without touching the membrane. The liquid was gently mixed by pipetting up and down 5 times. The cap was secured and the unit was centrifuged for 6 minutes at 13,000×g. The sample reservoir was separated from the collection tube and the flow-through was discarded. The YM-100 column was placed into the same collection tube and 200 μl of 1×TE buffer was added to the sample reservoir without touching the membrane. The liquid was gently mixed by pipetting up and down 5 times. The cap was secured and the unit was centrifuged for 6 minutes at 13,000×g. The sample reservoir was separated from the collection tube and the flow-through was discarded. The YM-100 column was placed into the same collection and 5 μl of 10 mM Tris, pH 8.0 was added to the sample reservoir without touching the membrane. The side of the reservoir was gently tapped to mix the liquid. The sample reservoir was placed upside down in a new collection tube and the entire assembly was centrifuged for 3 minutes at 13,000×g. The volume of cDNA collected in the bottom of the tube was about 5 µl and was diluted to 10 µl with RNase-free water.

Replicate amplifications were performed starting with 1 ng of total RNA or water alone (negative control). On average, 40-50 µg of amplified sRNA was recovered after amplifying 1 ng of total RNA vs. 0.2-0.5 µg of non-specific amplification product when using only water in the reverse transcription reaction in place of RNA.

Example 7

Each RNA sample was amplified as described in Example 5, except that the cDNA purification step was omitted, thus avoiding additional cDNA loss in the process. The cDNA purification step can be omitted because the terminal ribonucleotide on the 3' end of the reverse transcription primers cannot not be enzymatically extended with terminal deoxynucleotidyl transferase. Only the 3' end of the newly synthesized cDNA is extended with TdT. The following RNA/primer mix was prepared on ice:
   1-3 µl total RNA (not exceeding 2 ng)
   2 µl first round oligodT sequence specific RT primer (50 ng/µl) (5'-TAC AAG GCA ATT TTT TTT TTT TTT TTT V-3', where V=C, G or A ribonucleotides; SEQ ID NO: 10)
   1 µl first round random sequence specific RT primer (2× by mass of RNA) (5'-TAC AAG GCA ATT NNN NNN NNN-3', where the first 8 N=A, G, C or T deoxyribonucleotides at random and the final N=A, G, C or U ribonucleotides at random; SEQ ID NO: 11)
   RNase-free water to 5 µl The RNA/primer mixture was heated at 80° C. for 10 minutes and immediately cooled on ice for 1-2 min. The mixture was then mixed with 5.5 µl of a Master Mixture solution to bring the final volume to 10.5 µl containing 1×RT buffer (50 mM Tris-HCl (pH 8.3), 75 mM KCl, 3 mM MgCl$_2$), 10 mM dithiothreitol (DTT), 0.5 mM each dNTP, 10 U Superase-In™ (Ambion), and 200 U Superscript™ II reverse transcriptase (Invitrogen). The mixture was briefly centrifuged and incubated at 42° C. for 2 hrs. The first strand cDNA molecules were then tailed and further processed as described in Example 1.

Replicate amplifications were performed starting with 1 ng of total RNA or water alone (negative control). On average, 55-60 µg of amplified sRNA was recovered after amplifying 1 ng of total RNA vs. 0.2-0.5 µg of non-specific amplification product when using only water in the reverse transcription reaction in place of RNA.

Example 8

Each RNA sample was amplified as described in Example 7, except that the reverse transcriptase was not heat inactivated following second round cDNA synthesis and T3 promoter oligonucleotide was not added to the second round cDNA reaction. Rather, excess T7T3 promoter template from the first round promoter synthesis reaction binds to the 3' ends of the second round cDNA molecules, allowing the DNA-dependent DNA polymerase activity of the still-active reverse transcriptase to regenerate the double-stranded T7 promoter adjacent to the T3 sequences (see FIG. 3f).

Following first round sRNA synthesis as described in Example 1, 25 µl of sRNA was mixed with 1 µl second round sequence specific RT primer (500 ng/µl) (5'-TAC AAG GCA ATT-3'; SEQ ID NO: 7) and heated at 80° C. for 10 min. The reaction was immediately iced for 2 min, briefly centrifuged, and returned to ice. One µl dNTP mix (10 mM each) and 1 µl Superscript™ II reverse transcriptase (200 U/µl) was added, and the RT reaction incubated at 42° C. for 1 hr. One µl RNase H (2 U/µl) (Invitrogen) was added, and the reaction incubated at 37° C. for 30 min. The reaction was incubated at 65° C. to stop enzyme activity. In vitro transcription with T7 polymerase and sRNA purification and quantitation were then performed as described in Example 1.

Replicate amplifications were performed starting with 1 ng of total RNA or water alone (negative control). On average, 90-100 µg of amplified sRNA was recovered after amplifying 1 ng of total RNA vs. 0.2-0.5 µg of non-specific amplification product when using only water in the reverse transcription reaction in place of RNA.

Example 9

Tailing Procedure 1 is designed for use with standard labeling methods used with most spotted microarrays and in other gene expression assays (e.g., qRT-PCR). Tailing Procedue 2 is designed for use with downstream T7 amplification/labeling procedures, such as those recommended for Affymetrix GeneChip® microarrays Amersham CodeLink™ microarrays, Agilent Oligo microarrays, and OciChip™ microarrays.

PolyA Tailing Procedure 1

The desired volume of purified second round sRNA molecules was adjusted to 15.5 µl with nuclease-free water. For each tailing reaction, 10 mM ATP was diluted 1:50 in 1 mM Tris, pH 8.0 for each µg of sRNA in the reaction. PolyA polymerase (PAP) (2 U/µl) was diluted 1:5 in 1×PAP buffer (10 mM Tris-HCl, pH 7.0, 10 mM MgCl$_2$) and placed on ice until use. The sRNA solution was mixed with 9.5 µl of a Master Mixture solution to bring the final volume to 25 µl containing 1×PAP buffer, 2.5 mM MnCl, 0.2 mM ATP (per µg of sRNA), and 0.4 U polyA polymerase. The mixture was gently mixed, centrifuged and incubated in a 37° C. heat block for 15 min. The reaction was stopped by adding 3 µl 0.5 M EDTA. The tailed sRNA molecules were purified using the RNeasy MinElute™ Kit (Qiagen) following manufacturer's protocol for RNA cleanup and eluted in 14 µl RNase-free water. The recovered volume was approximately 12 µl.

PolyA Tailing Procedure 2

Ideally, 250-500 ng of second round sRNA is used in this polyA tailing procedure. However, it is not always possible to quantitate the sRNA from very small sample sizes. Therefore, the following table can be used to determine the amount of purified sRNA that should be used in the polyA tailing reaction:

|  | Amount of purified sRNA to use in the tailing reaction | |
| --- | --- | --- |
| Amount of RNA used in the first round | If dT primer was used for cDNA synthesis | If random primer or random and dT primers were used for CDNA synthesis |
| >100 ng | 500 ng* | 500 ng* |
| 100 ng | 3 µl | 500 ng* |
| 50 ng | 6 µl | 500 ng* |
| 25 ng | 12 µl | 2 µl |
| 10 ng | 12 µl | 4 µl |
| 5 ng | 12 µl | 8 µl |
| 2.5 ng | 12 µl | 12 µl |

*Sufficient amounts of sRNA should be available to confirm concentration via OD 260/280 measurements.

The appropriate volume of purified second round sRNA molecules was adjusted to 15.5 µl with nuclease-free water. For each tailing reaction, 10 mM ATP was diluted 1:100 in 1 mM Tris, pH 8.0. PAP (2 units per microliter) was diluted 1:5 in 1×PAP buffer and placed on ice until use. The sRNA solution was mixed with 9.5 µl of a Master Mixture solution to bring the final volume to 25 µl containing 1×PAP buffer, 2.5 mM MnCl, 0.2 mM ATP (per µg of sRNA), and 0.4 U polyA polymerase. The mixture was gently mixed, centrifuged and incubated in a 37° C. heat block for 15 min. The reaction was stopped by adding 3 µl 0.5 M EDTA. The tailed sRNA molecules were purified using the RNeasy MinElute™ Kit (Qiagen) following manufacturer's protocol for RNA cleanup and eluted in 14 µl RNase-free water. The recovered volume was approximately 12

Example 10

A kit for performing multiple rounds of sRNA synthesis was assembled with the following components:
  First Round Oligo dT Sequence Specific RT Primer (50 ng/µl);
  First Round Random Sequence Specific RT Primer (250 ng/µl);
  dNTP Mix (10 mM each dATP, dCTP, dGTP, dTTP);
  Superase-In™ RNase Inhibitor (Ambion);
  10 mM dATP;
  10× Reaction Buffer (100 mM Tris-HCl, pH 7.0, 100 mM $MgCl_2$);
  Terminal Deoxynucleotidyl Transferase (7.5 U/µl);
  T7T3 RNA Polymerase Promoter Template (50 ng/µl);
  Klenow Enzyme (2U/µl);
  rNTP Mix (ATP, GTP, CTP, and UTP) (75 mM each);
  10× RNA Polymerase Reaction Buffer (Ambion);
  T7 Enzyme Mix (Ambion);
  Second Round Sequence Specific RT Primer (500 ng/µl);
  T3 Promoter Oligonucleotide (50 ng/µl); and
  T3 Enzyme Mix (Ambion).

The components were placed in numbered vials and placed in a container with a printed instruction manual for multiple rounds of sRNA synthesis using the kit components.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed:

1. A method for performing multiple rounds of synthesis of at least one sRNA molecule, comprising:
   a) providing at least one first round single stranded cDNA molecule having a 5' end and a 3' end;
   b) attaching an oligodeoxynucleotide tail onto the 3' end of said first round cDNA molecule;
   c) annealing to said oligodeoxynucleotide tail a single stranded promoter template comprising a first RNA polymerase recognition sequence and at least a second different RNA polymerase recognition sequence 3' to said first recognition sequence, wherein said single stranded promoter template is not extendable with DNA polymerase;
   d) extending said oligodeoxynucleotide tail such that said single stranded promoter template is converted into a first RNA polymerase promoter and at least a second RNA polymerase promoter 3' to said first promoter;
   e) initiating a first round of RNA transcription using an RNA polymerase which recognizes said first RNA polymerase promoter to produce at least one first round sRNA molecule;
   f) synthesizing at least one second round single stranded cDNA molecule from said first round sRNA molecule, said second round single stranded cDNA molecule having 5' and 3' ends;
   g) degrading said first round sRNA molecule;
   h) annealing a single stranded promoter oligonucleotide complementary to said second different RNA polymerase recognition sequence such that a second RNA polymerase promoter is formed; and
   i) initiating a second round of RNA transcription using an RNA polymerase which recognizes said second RNA polymerase promoter to produce at least one second round sRNA molecule,
thereby performing multiple rounds of synthesis of at least one sRNA molecule and producing multiple sRNA copies.

2. The method of claim 1, wherein a) comprises providing a RNA molecule having 5' and 3' ends; and synthesizing a single stranded cDNA molecule from said RNA molecule.

3. The method of claim 2, wherein synthesis of the single stranded cDNA molecule comprises contacting the RNA molecule with a primer in the presence of a reverse transcriptase.

4. The method of claim 3, wherein the primer is selected from the group consisting of oligodT primer, random primer, and combinations thereof.

5. The method of claim 4, wherein the primer comprises a 5' extension containing a specific nucleotide sequence.

6. The method of claim 4, wherein the 3' terminal nucleotide of the primer is not a substrate for terminal deoxynucleotide transferase but can be extended by reverse transcriptase.

7. The method of claim 6, wherein the 3' terminal nucleotide of the primer is a ribonucleotide.

8. The method of claim 4, wherein the primer comprises a 5' extension containing a specific nucleotide sequence, wherein the 3' terminal nucleotide of said primer is a ribonucleotide.

9. The method of claim 1, wherein the single stranded promoter template comprises a first RNA polymerase recognition sequence selected from the group consisting of T7, T3 and SP6 RNA polymerase recognition sequence, a second RNA polymerase recognition sequence selected from the group consisting of T7, T3 and SP6 RNA polymerase recognition sequence, and optionally a third RNA polymerase recognition sequence selected from the group consisting of T7, T3 and SP6 RNA polymerase recognition sequence, wherein said first, second and optionally third RNA polymerase recognition sequences are different.

10. The method of claim 1, wherein f) comprises contacting the first round sRNA molecule with a primer in the presence of reverse transcriptase.

11. The method of claim 10, wherein the reverse transcriptase is RNase H⁻.

12. The method of claim 10, wherein the reverse transcriptase is RNase H⁺ and wherein the RNase H⁺ activity degrades the first round sRNA molecule in g).

13. The method of claim 10, wherein reverse transcriptase activity in f) is inactivated prior to initiation of second round RNA transcription in i).

14. The method of claim 10, wherein the primer is selected from the group consisting of oligodT primer, random primer, and combinations thereof.

15. The method of claim 5, wherein f) comprises contacting the sRNA molecule with a second primer in the presence of reverse transcriptase, wherein said second primer comprises a nucleotide sequence corresponding to the specific nucleotide sequence contained in the 5' extension of the first primer.

16. The method of claim 5, wherein the primer is selected from the group consisting of oligodT primer, random primer, and combinations thereof.

17. The method of claim 1, further comprising reverse transcribing the resulting multiple sRNA copies, thereby producing multiple single stranded cDNA molecules.

18. The method of claim 1, further comprising adding polyA tails to the resulting multiple sRNA copies.

19. A method for performing multiple rounds of synthesis of at least one sRNA molecule, comprising:
   a) providing at least one first round single stranded cDNA molecule having a 5' end and a 3' end;
   b) attaching an oligodeoxynucleotide tail onto the 3' end of said first round single stranded cDNA molecule;
   c) annealing to said oligodeoxynucleotide tail a single stranded promoter template comprising a first RNA polymerase recognition sequence and at least a second different RNA polymerase recognition sequence 3' to said first recognition sequence, wherein said single stranded promoter template is not extendable with DNA polymerase;
   d) extending said oligodeoxynucleotide tail such that said single stranded promoter template is converted into a first RNA polymerase promoter and at least a second RNA polymerase promoter 3' to said first promoter;
   e) initiating a first round of RNA transcription using an RNA polymerase which recognizes said first RNA polymerase promoter to produce at least one first round sRNA molecule;
   f) synthesizing at least one second round single stranded cDNA molecule from said first round sRNA molecule, said second round single stranded cDNA molecule having 5' and 3' ends;
   g) degrading said first round sRNA molecule;
   h) annealing excess single stranded promoter template from step c) to the 3' end of said second round cDNA molecule;
   i) extending the 3' end of said second round cDNA molecule such that said excess single stranded promoter template is converted into a first RNA polymerase promoter and at least a second RNA polymerase promoter 3' to said first promoter; and
   j) initiating a second round of RNA transcription using an RNA polymerase which recognizes said first or second RNA polymerase promoter to produce at least one second round sRNA molecule,
thereby performing multiple rounds of synthesis of at least one sRNA molecule and producing multiple sRNA copies.

20. The method of claim 19, wherein enzyme activity in i) is inactivated prior to initiation of second round RNA transcription in j).

* * * * *